US00PP31447P2

(12) United States Plant Patent
Bourne

(10) Patent No.: US PP31,447 P2
(45) Date of Patent: Feb. 18, 2020

(54) GRAPEVINE NAMED 'SV31-16-10'

(50) Latin Name: *Vitis vinifera*
Varietal Denomination: SV31-16-10

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 16/350,207

(22) Filed: Oct. 11, 2018

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812
See application file for complete search history.

*Primary Examiner* — Kent L Bell
(74) *Attorney, Agent, or Firm* — Baker Manock & Jensen, PC; Eric C. Cole

(57) ABSTRACT

A new and distinct variety of grapevine plant named 'SV31-16-10' particularly characterized by natural berries which are ellipsoidal in shape, seedless, reddish black to black skinned berries which are medium large, sweet, with a neutral flavor and which have thin skins and crisp texture. Clusters of berries of grapevine plant named 'SV31-16-10' are very responsive to exogenous gibberellic acid applications and trunk girdling. Berry shape of clusters treated with gibberellic acid is obovate (see FIG. 2) and clusters are large, well-filled and loose, producing berries averaging 9.5 g in mass.

3 Drawing Sheets

Latin name of the genus and species of the plant claimed: The plant claimed relates to a new and distinct variety of *Vitis vinifera*.

Variety denomination: The plant claimed shall be known as 'SV31-16-10'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV31-16-10'. As used herein, 'grapevine' refers to all plant parts including, vines, canes, tendrils, leaves, fruit and roots of 'SV31-16-10'. This new cultivar originated from a cross conducted in May 2010 near McFarland, Calif. between the seedless selection 'SV19-28-303' (unpatented) and pollen parent 'SV16-72-83' (unpatented). Clusters of fruit resulting from the hybridization were harvested six weeks after crossing and the resultant ovules were cultured on 'McCown's Woody Plant Medium' at a temperature of 22° C. for twelve weeks. Subsequently, the resultant embryonic plants were cultured in the same medium in the laboratory under twelve hours of light from standard fluorescent lamps at 26.4° C. The seedlings were then planted in a standard greenhouse flat and were grown in the greenhouse at 26.4° C. with 12 hours' illumination under high pressure sodium vapor lamps. The seedling population of 58 plants was planted in an irrigated field in the spring of 2011 near Delano, Calif.

The new grapevine was selected from this seedling population on Aug. 26, 2014. It was then propagated by woody cuttings and bench grafted to 'Freedom' (unpatented) rootstock in 2015. The present invention has been found to retain its distinctive characteristics through two successive asexual propagations of woody cuttings.

Grapevine named 'SV31-16-10' differs from its female parent grapevine 'SV19-28-303' (not patented) in that grapevine named 'SV31-16-10' has ellipsoidal dark reddish black to black berries with crisp texture and a small seed trace while female parent grapevine 'SV19-28-303' has reddish black berries with meaty texture and a large seed trace of woody cuttings.

Grapevine named 'SV31-16-10' differs from its male parent 'SV16-72-83' (unpatented) in that grapevine named 'SV31-16-10' has berries which are ellipsoidal with small seed traces while male parent 'SV16-72-83' has berries with a large, partially sclerified seed traces and a more irregular shaped berry than the extant cultivar.

Grapevine named 'SV31-16-10' differs from the commercial cultivar 'IFG Six' (U.S. Plant Pat. No. 23,531) in that grapevine named 'SV31-16-10' has berries which, when treated with 10 ppm exogenous gibberellic acid, have a larger diameter and obovate shaped berries (see FIG. 2) which ripen in mid August while 'IFG-Six' (U.S. Plant Pat. No. 23,531) produces elongate, tubular shaped berries with a smaller diameter which ripen in late August to early September. Additionally, grapevine named 'SV31-16-10' produces a few berries with dimpled tips while 'IFG Six' (U.S. Plant Pat. No. 23,531) produces berries which are generally dimpled. Under commercial growing conditions, the berry shape of grapevine named 'SV31-16-10' becomes obovate in outline compared to the natural fruit which is ellipsoidal in outline.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. Reddish black to black berry color;
2. Firm texture; and
3. Medium sized berries with a sweet, neutral taste and thin skin.
4. Berries which are very responsive to gibberellic acid applications and girdling, often producing berries which exceed a mass of 10 g.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The first photograph is of a single cluster of fruit found on the seedling vine in August of 2014 near Delano, Calif. The second photo is one of shoots, leaves and a fruit cluster taken from a two year old plant grown in a field near Bakersfield, Calif. in 2018. The third photograph was taken in 2018 and illustrates fruit on a 3.5 year old vine, grown in a field near McFarland, Calif.

DETAILED BOTANICAL DESCRIPTION

Figure 1:
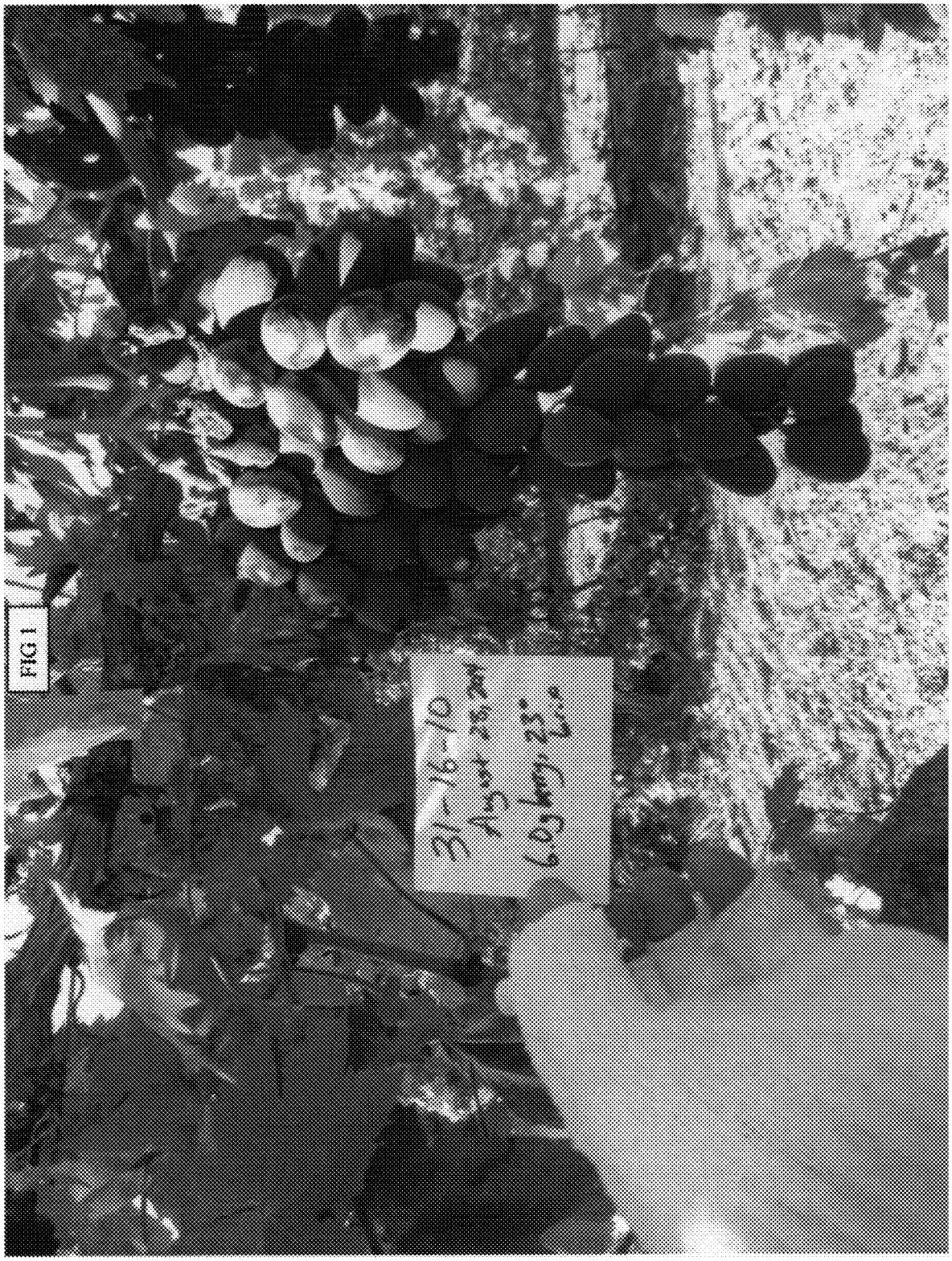
FIG. 1 Fruit cluster on seedling vine.
Figure 2:
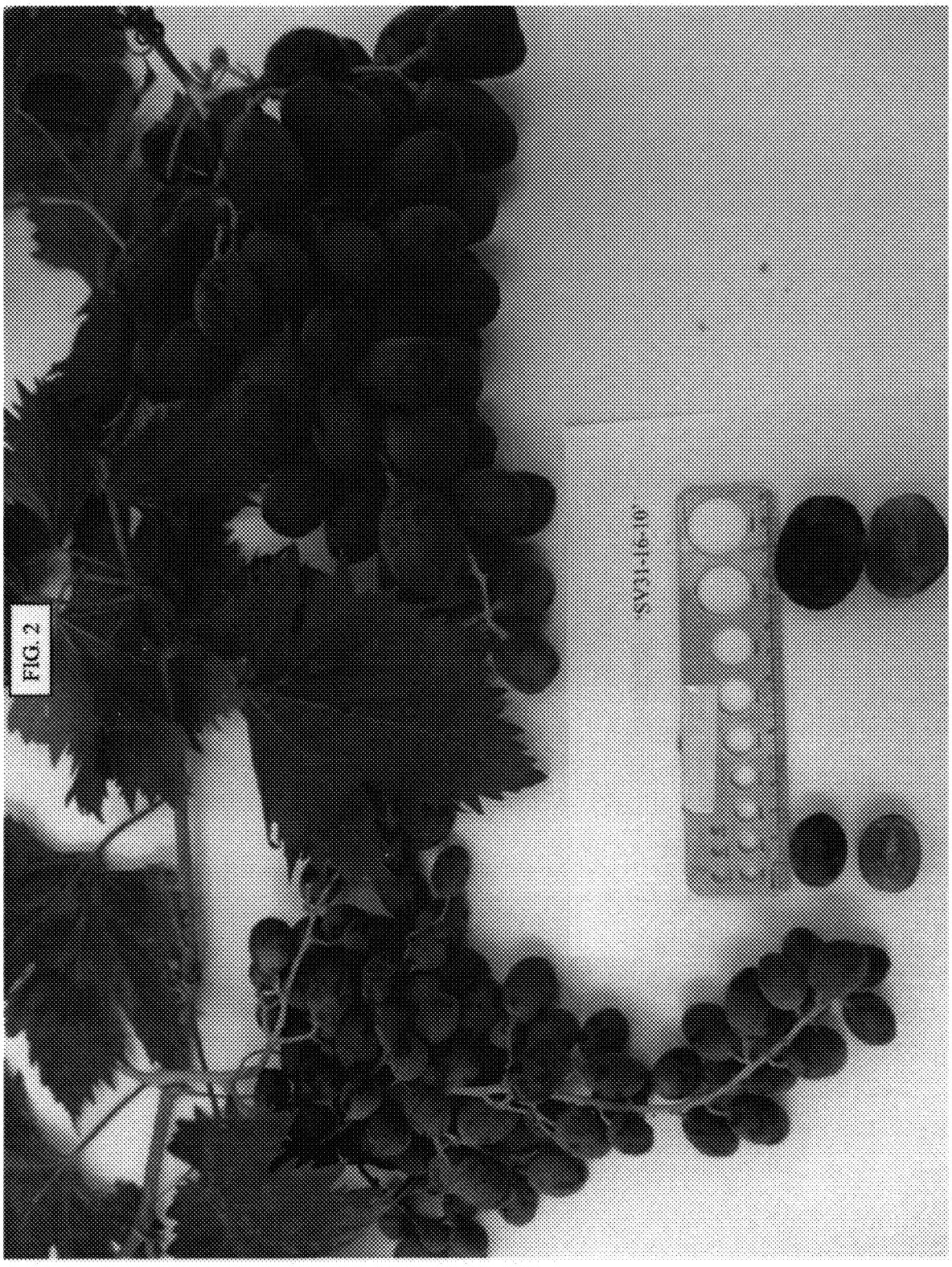
FIG. 2 Fruit, shoots and leaves of a two year old vine.
Figure 3:
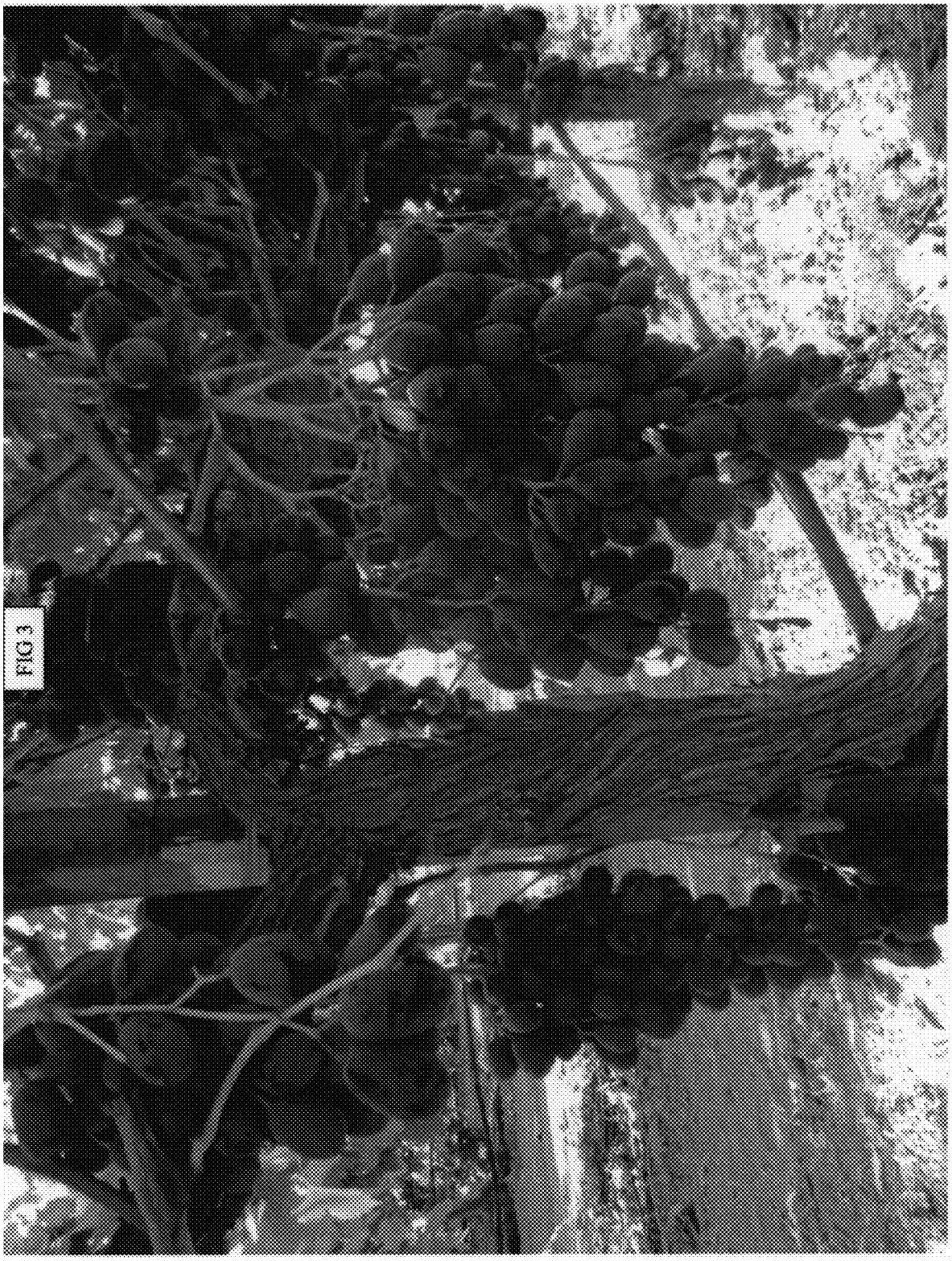
FIG. 3. Fruit on a 3.5 year old vine.

The following detailed description sets forth the distinctive characteristics of grapevine named 'SV31-16-10'. Descriptions of the new invention apply to vines of grapevine named 'SV31-16-10' grown on 'Freedom' (unpatented) rootstock at a density of 1,537 vines per hectare grown near McFarland, Calif. in 2018. These vines were in their second year of full production, having been planted in 2015. These descriptions are believed to apply generally to the new variety grown under similar circumstances elsewhere. Deviation from some characteristics can be expected when cropping levels are greater than those described herein. References to color correspond to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV31-16-10'.

Plant:

*Vigor*.—High; canes averaging 288 cm. on vines spur-pruned and shoot thinned to 32 shoots.
*Density of foliage*.—Medium.
*Productivity*.—Very productive when pruned to spurs with canes, up to 32,000 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.
*Inner bark color*.—RHS Greyed orange group 175D.
*Outer bark color*.—RHS Brown group N200B.

Growing tips:

*Apex*.—Open.
*Density of prostrate hairs on tip*.—Moderate.
*Density of erect hairs on tip*.—Absent.
*Color*.—RHS Yellow Green Group 144B.
*Anthocyanins*.—Absent.
*Shape*.—Flattened.
*Shoot attitude*.—Erect.

Young shoot:

*Density of erect hairs on node*.—Absent.
*Density of erect hairs on internode*.—Absent.
*Density of prostrate hairs on node*.—Sparse.
*Density of prostrate hairs on internode*.—Sparse.
*Internode color, lower surface*.—RHS Yellow green group 146C.
*Internode color, upper surface, in sun*.—RHS Red purple group 61B.

Young leaves:

*Density of erect hairs on node*.—Absent.
*Density of erect hairs on internode*.—Absent.
*Density of prostrate hairs on node*.—Absent.
*Density of prostrate hairs on internode*.—Sparse.
*Internode color, lower surface*.—RHS Yellow green group 144A.
*Color of young leaves*.—RHS Green group 143A.
*Density of prostrate hairs, lower surface, between veins*.—Absent.
*Density of erect hairs lower blade surface, between veins*.—Sparse, found only at base of main veins.
*Density of prostrate hairs on main veins, lower surface*.—Sparse.

Mature leaves:

*Average blade length*.—16.1 cm.
*Average blade width*.—17.8 cm.
*Size of blade*.—Large.
*Shape*.—Pentagonal.
*Anthocyanin coloration of main veins on the upper side of the blade*.—Present in some leaves well-exposed to the sun: RHS Red purple group 59B.
*Mature leaf profile*.—Undulating.
*Blistering* (*upper surface*).—Absent.
*Leaf blade tip*.—Apex points downward.
*Margins*.—Lobed, serrated, undulating.
*Apex*.—Narrowly acuminate.
*Bases*.—Hastate.
*Thickness*.—Medium.
*Undulation of blade between main and lateral veins*.—Slight.
*Shape of teeth*.—Conical; both sides convex.
*Length of teeth*.—3-12 mm.
*Ratio length/width of teeth*.—Variable, generally slightly longer than wide.
*General shape of petiole sinus*.—Wide open; ovate in outline.
*Tooth at petiole sinus*.—Absent.
*Petiole sinus limited by veins*.—Absent.
*Shape of upper lateral sinus*.—Closed.

*Prostrate hairs between veins* (*lower surface*).—Absent.

*Erect hairs between veins* (*lower surface*).—Absent.

*Prostrate hairs on main veins* (*lower surface*).—Absent.

*Density of erect hairs on main veins* (*lower surface*) .—Sparse, limited to junction of veins.

*Prostrate hairs on main veins* (*upper surface*).—Absent.

*Prostrate hairs between veins* (*upper surface*).—Absent.

*Upper surface*.—Summer color: RHS Green group 137C. Surface texture: Smooth. Surface appearance: Dull. Goffering of blade: Absent.

*Lower surface*.—Summer color: RHS Green group 143B. Anthocyanin coloration of main veins on lower leaf surface: Present on some leaves well exposed to the sun: RHS Red purple group 59C. Anthocyanin coloration on laterals: No. Glossiness: Low. Surface texture: Rough. Surface appearance: Dull.

*Petiole*.—Diameter (typical): 2 mm. Diameter (observed): 2 mm. Length: 11.2 cm. Length of petiole compared to middle vein: Much shorter. Density of prostrate hairs: Absent. Density of erect hairs: Absent. Shape of base of petiole sinus: Wide open. Color: In shade: RHS Yellow green group 144C. In sun: RHS Red purple group 59C.

Tendrils:

*Length* (*typical*).—23 cm.

*Length* (*observed*).—23 cm.

*Diameter* (*typical*).—1 mm.

*Diameter* (*observed*).—1 mm.

*Color*.—In shade: RHS Yellow green group N144B.

*Form*.—Bifurcated or trifurcated.

*Number of successive tendrils*.—At most, 2.

*Density of prostrate hairs*.—Absent.

Flowers:

*Flower sex*.—Perfect.

*Position of first flowering nodes*.—Fourth or fifth.

*Number of inflorescences per shoot*.—Usually one.

*Length of inflorescence*.—19 cm.

*Calypta color*.—RHS Green group 141C.

*Ovary length*.—3 mm.

*Ovary width*.—1.5 mm.

*Ovary color*.—RHS Green group N134A.

*Filament length*.—1.5 mm.

*Filament color*.—Translucent — no pigmentation.

*Anther length*.—1 mm.

*Anther color*.—RHS Yellow group 8C. Date of full bloom: May $11^{th}$.

Fruit:

*Ripening period*.—Mid-season.

*Date of ripening*.—August 15th at McFarland, Calif.

*Date of first harvest*.—August 15 at McFarland, Calif.

*Use*.—Fresh market.

*Keeping quality*.—Good.

*Shipping quality*.—Good.

*Solids-sugar*.—20.5 brix at full maturity.

*Cluster*.—

*Bunch*.—Natural Bunch. Size: Large. Length (peduncle excluded): 37.4 cm. Width: 14.8 cm. Weight: 553 g. Density: Well-filled, but loose. Number of berries: 153. Bunch on vines treated with gibberellic acid and trunk girdled: Length: 23 cm. Width: 16 cm. Weight: 998 g. Density: Well-filled, loose. Number of berries: 104. Form: Cylindrical with an occasional long shoulder.

*Peduncle*.—Length (typical): 3.1 cm. Length (observed): 3.1 cm. Width (typical): 7 mm. Width (typical): 7 mm. Lignification: About 2 cm. at base. Color: RHS Yellow green group 144A.

*Pedicel*.—Length: Variable about 1.0 to 1.5 cm. Width: About 2 mm. Color: RHS Yellow green group 144B.

*Berry*.—Natural berries: Berry skin color: RHS Red purple group 59A to RHS Black group 202A. Berry flesh color: Yellow green group 145C. Size: Medium large. Weight: 3.4 g. Shape: Elliptical. Gibberellic acid treated berries. Size: Very large. Weight: 9.5 g. Shape: Obovate, some berries with dimpled tips. Presence of seeds: Seedless; most berries develop one or two tiny ovule traces about 3-5 mm in length. Cross section: Circular. Dimensions: Natural berry: Longitudinal axis: About 2.5 cm. Horizontal axis: About 1.3 cm. Gibberellic acid treated berries. Longitudinal axis: About 3.4 cm. Horizontal axis: About 2.5 cm. Skin color (without bloom): In shade of canopy: RHS Red purple group 59A. In clusters exposed to the sun: RHS Black group 202A. Juiciness of flesh: Very juicy. Flesh texture: Crisp. Berry firmness: Very firm. Particular flavor: Neutral. Bloom (cuticular wax): Heavy. Pedicel length: Variable, 7-12 mm. Berry separation from pedicel: Difficult. Skin: Thickness: Thin. Reticulation: Absent. Roughness: Absent. Tenacity: Tenacious to flesh. Tendency to crack: Resistant.

Mature cane color: Greyed orange 172B.

Disease and insect resistance: Moderately susceptible to powdery mildew which may be controlled with standard fungicides in California.

Having thus described and illustrated our new variety of grapevine:

1. A new and distinct variety of grapevine plant named 'SV31-16-10' substantially as illustrated and described herein.

* * * * *